(12) United States Patent
Megerman et al.

(10) Patent No.: US 7,238,184 B2
(45) Date of Patent: Jul. 3, 2007

(54) ABLATION PROBE WITH PELTIER EFFECT THERMAL CONTROL

(75) Inventors: Joseph Megerman, Brookline, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 449 days.

(21) Appl. No.: 10/802,092

(22) Filed: Mar. 15, 2004

(65) Prior Publication Data

US 2005/0203505 A1    Sep. 15, 2005

(51) Int. Cl.
A61B 18/14    (2006.01)
A61B 18/02    (2006.01)

(52) U.S. Cl. .............................. 606/41; 606/20; 606/21
(58) Field of Classification Search ................... 606/41, 606/20–21
See application file for complete search history.

(56) References Cited

U.S. PATENT DOCUMENTS

| | | | | |
|---|---|---|---|---|
| 4,860,748 | A * | 8/1989 | Chiurco et al. | 607/96 |
| 5,139,496 | A * | 8/1992 | Hed | 606/23 |
| 5,529,067 | A * | 6/1996 | Larsen et al. | 600/374 |
| 5,735,846 | A * | 4/1998 | Panescu et al. | 606/41 |
| 5,755,752 | A * | 5/1998 | Segal | 607/89 |
| 5,779,696 | A * | 7/1998 | Berry et al. | 606/16 |
| 5,951,546 | A | 9/1999 | Lorentzen | |
| 6,196,839 | B1 * | 3/2001 | Ross | 433/3 |
| 6,212,433 | B1 * | 4/2001 | Behl | 607/101 |
| 6,379,353 | B1 | 4/2002 | Nichols | |
| 6,427,089 | B1 | 7/2002 | Knowlton | |
| 6,547,783 | B1 * | 4/2003 | Vilendrer et al. | 606/20 |
| 6,575,967 | B1 | 6/2003 | LeVeen et al. | |
| 6,685,702 | B2 * | 2/2004 | Quijano et al. | 606/41 |
| 2003/0014098 | A1 * | 1/2003 | Quijano et al. | 607/122 |
| 2004/0079089 | A1 * | 4/2004 | Wallach | 62/3.2 |

OTHER PUBLICATIONS

PCT International Search Report for PCT/US2005/003588, Applicant: Boston Scientific Scimed, Inc., Forms PCT/ISA/210 and 220, dated Apr. 28, 2005 (9 pages).
PCT Written Opinion of the International Search Authority for PCT/US2005/003588, Applicant: Boston Scientific Scimed, Inc., Form PCT/ISA/237, dated Apr. 28, 2005 (4 pages).

* cited by examiner

*Primary Examiner*—Michael Peffley
*Assistant Examiner*—Alex Toy
(74) *Attorney, Agent, or Firm*—Vista IP Law Group LLP

(57) ABSTRACT

A tissue ablation probe, system, and method are provided. The ablation probe comprises an elongated member, an ablative element mounted on the distal end of the elongated member, and at least one thermoelectric device mounted to the member in thermal communication with the ablative element. The system may include the ablation probe, thermal control circuitry for controlling the thermal effect of the thermoelectric device, and an ablation source for supplying ablation energy to the ablative element. A plurality of circumferentially distributed thermoelectric devices can be provided, so that radial tissue sectors can be selectively affected by independently controlling the thermal effect of the thermoelectric devices. In one embodiment, the thermoelectric device(s) can be used to cool a heat ablative element. In another embodiment, the thermoelectric device(s) can be used to heat an ablative element, thereby forming a heat ablative element. In still another embodiment, the thermoelectric device(s) can be used to cryogenically cool an ablative element, thereby forming a cryogenic ablative element.

34 Claims, 10 Drawing Sheets

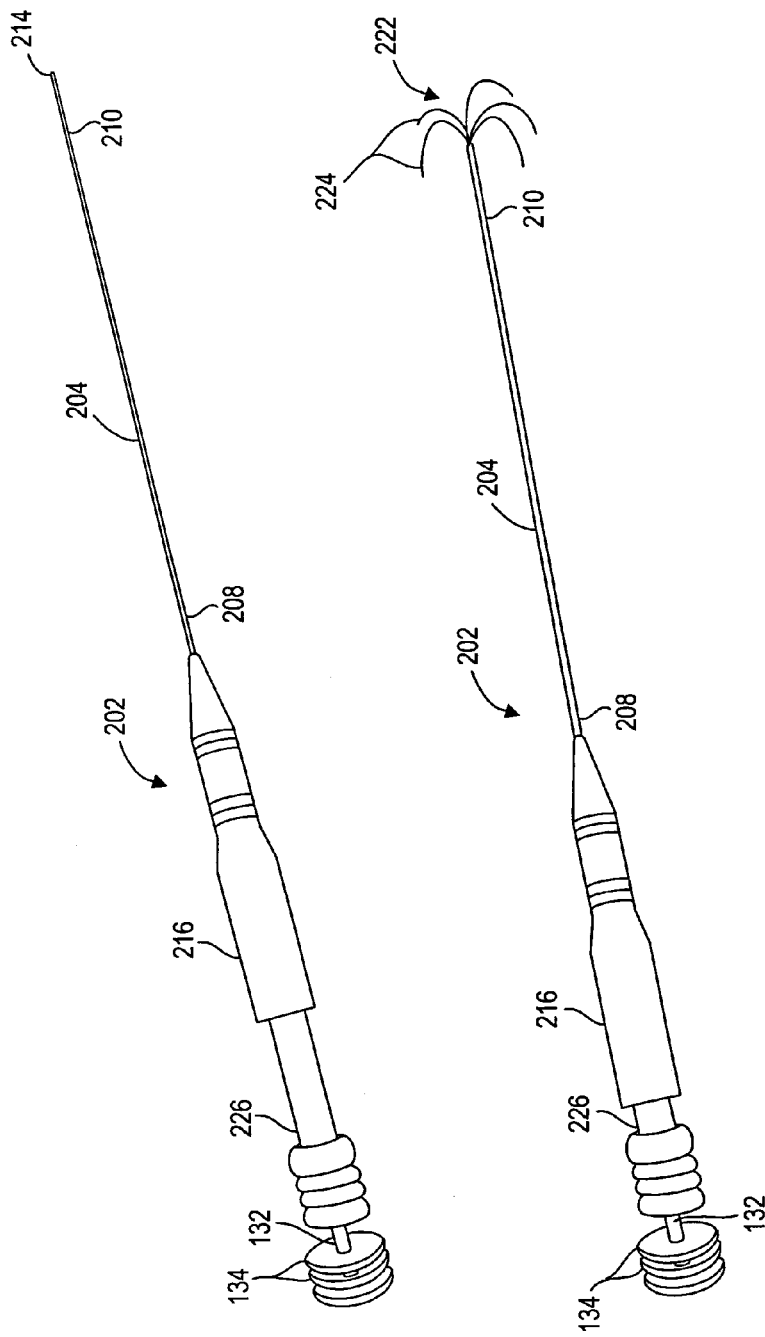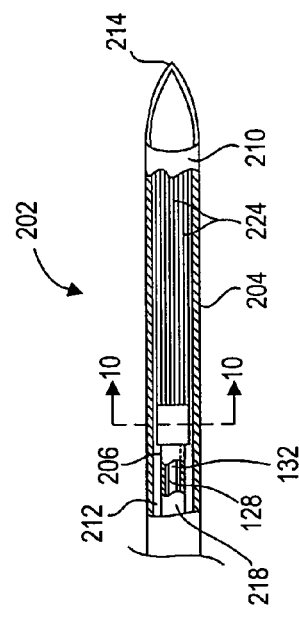
Fig. 7
Fig. 8
Fig. 9

ABLATION PROBE WITH PELTIER EFFECT THERMAL CONTROL

TECHNICAL FIELD

The present invention relates generally to medical devices for thermal energy ablation procedures.

BACKGROUND OF THE INVENTION

Tissue may be destroyed, ablated, or otherwise treated using thermal energy during various therapeutic procedures. Many forms of thermal energy may be imparted to tissue, such as radio frequency (RF) electrical energy, microwave electromagnetic energy, laser energy, acoustic energy, or thermal conduction. In one particular application, RF energy may be delivered to diseased regions (e.g., tumors) for the purpose of ablating predictable volumes of tissue with minimal patient trauma. RF ablation of tumors is currently performed using one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. In theory, RF ablation can be used to uniformly sculpt the volume of necrosis to match the extent of the tumor. By varying the power output and the type of electrical waveform, it is theoretically possible to control the extent of heating, and thus, the resulting ablation. The diameter of tissue coagulation from a single electrode, however, is limited by heat dispersion. As a result, multiple probe insertions have been required to treat all but the smallest lesions. This considerably increases treatment duration and requires significant skill for meticulous precision of probe placement.

The second technology utilizes multiple needle electrodes, which have been designed for the treatment and necrosis of tumors in the liver and other solid tissues. U.S. Pat. No. 6,379,353 discloses such a probe, which is commercially available as the LeVeen Needle Electrode. This probe comprises a cannula having a needle electrode array, which is reciprocatably mounted within the cannula to alternately deploy the electrode array from the cannula and retract electrode array within the cannula. The individual electrodes within the array have spring memory, so that they assume a radially outward, arcuate configuration as they are deployed from the cannula. In general, a multiple electrode array creates a larger lesion than that created by a single needle electrode.

Whichever technology is utilized, increasing generator output has been unsuccessful for increasing lesion diameter, because an increased wattage is associated with a local increase of temperature to more than 100° C., which induces tissue vaporization and charring. This then increases local tissue impedance, limiting RF deposition, and therefore heat diffusion and associated coagulation necrosis.

To reduce the local temperature, thereby minimizing tissue vaporization and charring, the needle electrode or electrodes can be cooled. With regard to the single needle technology, two coaxial lumens may currently be provided in the needle electrode, one of which is used to deliver a cooled saline (e.g., room temperature or cooler) to the tip of the electrode, and the other of which is used to return the saline to a collection unit outside of the body. See, e.g., Goldberg et al., Radiofrequency Tissue Ablation: Increased Lesion Diameter with a Perfusion Electrode, Acad Radiol, August 1996, pp. 636-644.

Although the circulation of a cooled fluid through the needle electrode provides for a more efficient means for creating a lesion, it requires additional equipment in the form of a pump and collection reservoir. In addition, uniform lesions are not always created even when the needle electrodes are cooled, because the vascular heating sinking effect often pulls heat away from adjacent tissue that is being ablated.

There thus remains a need to provide an improved method, apparatus, and system for cooling tissue during an ablation procedure.

SUMMARY OF THE INVENTION

In accordance with a first aspect of the present invention, an ablation probe comprises an elongated member, which is preferably rigid or semi-rigid, so that it can be introduced through solid tissue. The ablation probe, however, can be flexible without straying from the principles taught by this invention. The ablation probe further comprises an ablative element. In one preferred embodiment, the ablative element is a tissue-penetrating electrode, such that the ablation probe can be more easily introduced through solid tissue. In another preferred embodiment, a plurality of tissue-penetrating needle electrodes can be provided. In this case, the needle electrodes can be deployable from, e.g., a cannula.

The ablation probe further comprises at least one thermoelectric device mounted to the elongated member in thermal communication with the ablative element. The thermoelectric device(s) may be in direct contact with the ablative element, but need not be as long as there is thermal communication. The thermoelectric device(s) can be conveniently operated merely by transmitting signals, e.g., applying a direct current (DC), to the thermoelectric device (s).

The thermoelectric device(s) can be configured in a variety of manners, depending on the nature of the ablative element and whether tissue is to be hyperthermically or hypothermically ablated. For example, if the ablative element is a heat ablative element having an independent heating means, such as a radio frequency (RF) electrode, the thermoelectric device(s) can be used to cool the heat ablative element during the ablation process, thereby providing for a more efficient ablation. The thermoelectric device(s) can optionally be used to pre-heat the heat ablative element. This cooling and pre-heating functionality can be combined into a single ablation probe merely by switching the polarity of signals transmitted to the thermoelectric devices. The thermal nature of the ablative element can also be dictated by the thermoelectric device(s). For example, the thermoelectric device(s) can be configured for cryogenically cooling the ablative element, so that the ablative element can hypothermically ablate tissue. Or the thermoelectric device(s) can be configured for heating the ablative element, so that the ablative element can hyperthermically ablate tissue. This cryogenic cooling and heating functionality can be combined into a single ablation probe merely by switching the polarity of signals transmitted to the thermoelectric devices.

If the thermoelectric device(s) are designed to cool the ablative element, whether to provide a more efficient hyperthermic ablation process, or to cryogenically cool the ablative element, the ablation probe may optionally comprise a heat sink thermally coupled to the thermoelectric device. In this case, the thermoelectric device(s) comprises a cold side in thermal communication with the ablative element and a hot side in thermal communication with the heat sink. Preferably, the heat sink comprises a heat sink rod that extends through the elongated member and cooling fins formed at a proximal end of the heat sink rod. Rather than using a separate heat sink, the thermoelectric device may take the form of an elongated tube that extends through the elongated member.

The ablation probe can be used in an ablation system that comprises thermal control circuitry electrically coupled to the thermoelectric device, and an ablation source (e.g., an RF ablation source) coupled to the ablative element. The control circuitry is configured for transmitting signals to the thermoelectric device(s), whereby the thermoelectric device (s) either cool or heat the ablative element, whichever the case may be. Optionally, the ablation system comprises a console that conveniently contains the thermal control circuitry and ablation source.

In accordance with a second aspect of the present invention, an ablation probe comprises a delivery cannula, which is preferably rigid or semi-rigid, but may be flexible. The ablation probe further comprises an inner probe member slidably disposed within a lumen of the cannula. In one preferred embodiment, the inner probe member is removable from the cannula, such that the cannula lumen can be used to deliver therapeutic agents prior or subsequent to the ablation process. The ablation probe further comprises a first tissue ablation electrode mounted to the distal end of the cannula, and a second tissue ablation electrode mounted to a distal end of the probe member, wherein the first and second electrodes are configured to be placed into a bipolar configuration. In one preferred embodiment, the second ablation electrode is a tissue-penetrating electrode, such that the ablation probe can be more easily introduced through solid tissue. In another preferred embodiment, the first and second ablation electrodes may be RF electrodes. The ablation probe further comprises a thermoelectric cooling device mounted either to the delivery cannula in thermal communication with the first electrode or to the inner probe member in thermal communication with the second electrode. The thermoelectric cooling device may be in direct contact with the respective electrode, but need not be as long as there is thermal communication.

In accordance with a third aspect of the present invention, an ablation probe comprises an elongated member and a heat ablative element mounted to the distal end of the elongated member. The structure of the elongated member and heat ablative element can be the same as previously described. The ablation probe further comprises a plurality of circumferentially distributed cooling devices in thermal communication with the ablative element. In one preferred embodiment, the cooling devices are thermoelectric cooling devices, but may take the form of other types of cooling devices also. The ablative element may optionally comprise a cylindrical portion, in which case, the cooling devices may be circumferentially distributed around the inner surface of the cylindrical portion. The ablation probe may optionally comprise a heat sink, which may have the same structure and association with the thermoelectric devices as previously described above.

The ablation probe can be used in an ablation system that comprises thermal control circuitry and an ablation source (e.g., an RF ablation source) coupled to the ablative element. The control circuitry is configured for independently controlling the respective cooling devices, whereby the cooling devices cool the ablative element. Optionally, the ablation system comprises a console that conveniently contains the thermal control circuitry and ablation source.

In accordance with a fourth aspect of the present invention, an ablation system comprises an elongated member and a heat ablative element mounted to the distal end of the elongated member. The structure of the elongated member and heat ablative element can be the same as previously described. The ablation system further comprises a plurality of thermoelectric cooling devices mounted to the elongated member in thermal communication with the ablative element, and thermal control circuitry electrically coupled to the thermoelectric device. The ablation system can have an ablation source (e.g., an RF ablation source) coupled to the ablative element. Optionally, the ablation system comprises a console that conveniently contains the thermal control circuitry and ablation source.

The control circuitry is configured for independently transmitting signals to the respective thermoelectric devices, whereby the thermoelectric devices heat the ablative element. For example, the thermal control circuitry may be configured to selectively turn certain thermoelectric devices off, so that they do not provide a cooling effect. This can be accomplished based on predetermined criteria (e.g., the tissue adjacent the thermoelectric device is already being cooled by a blood vessel), or based on a feedback signal, e.g., a tissue temperature or impedance signal. Alternatively, the thermal control circuitry is configured for cycling each thermoelectric device with a uniform duty cycle, e.g., to moderate the cooling effect of the thermoelectric devices. In this case, the thermal control circuitry can be configured for independently varying the uniform duty cycles of the thermoelectric devices, so that some provide a greater cooling effect than others. Or, the thermal control circuitry can be configured for independently transmitting signals with different amplitudes to the thermoelectric devices, so that some thermoelectric devices (e.g., those to which higher amplitude signals are supplied) provide a greater cooling effect than others.

In accordance with a fifth aspect of the present invention, a tissue ablation console comprises a tissue ablation source (e.g., an RF source) and thermal control circuitry configured for transmitting electrical signals to a thermoelectric device. If a plurality of thermoelectric devices are to be controlled, the thermal control circuitry may be configured for independently transmitting electrical signals to the thermoelectric devices. The thermal control circuitry may be configured to independently control the thermoelectric devices in the same manner described above.

In accordance with a sixth aspect of the present invention, a method of ablating tissue (e.g., abnormal tissue, such as a tumor) divided into a plurality of radial sectors is provided. The method comprises introducing a heating element adjacent an origin of the radial sectors, and radially conveying thermal energy from the heating element into the radial tissue sectors. In the preferred method, the tissue is ablated by the thermal energy conveyed from the ablative element. The method further comprises selectively cooling the radial tissue sectors. For example, a blood vessel may be contained within one or more of the radial tissue sectors, in which case, at least one of the one or or more radial tissue sectors is selectively not cooled or cooled less than the remaining radial tissue sectors. In the preferred method, this is accomplished with a plurality of discrete circumferentially distributed cooling devices, such as thermoelectric devices. The radial tissue sectors may be selectively cooled by turning off one or more cooling devices, so that they do not have a cooling effect during the ablation process. Or each of the cooling devices can be cycled with a uniform duty cycle, in which case, the duty cycles of the cooling devices can be selected to be different. Or each signals with different amplitudes can be transmitted to the cooling devices.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 7 is a perspective view of another ablation probe that can be used in the ablation system of FIG. 1, particularly showing a retracted electrode array;

FIG. 8 is a perspective view of the ablation probe of FIG. 7, particularly showing a the electrode array deployed;

FIG. 9 is a partially cutaway side view of the distal end of the ablation probe of FIG. 7;

DETAILED DESCRIPTION OF THE ILLUSTRATED EMBODIMENTS

Figure 1:
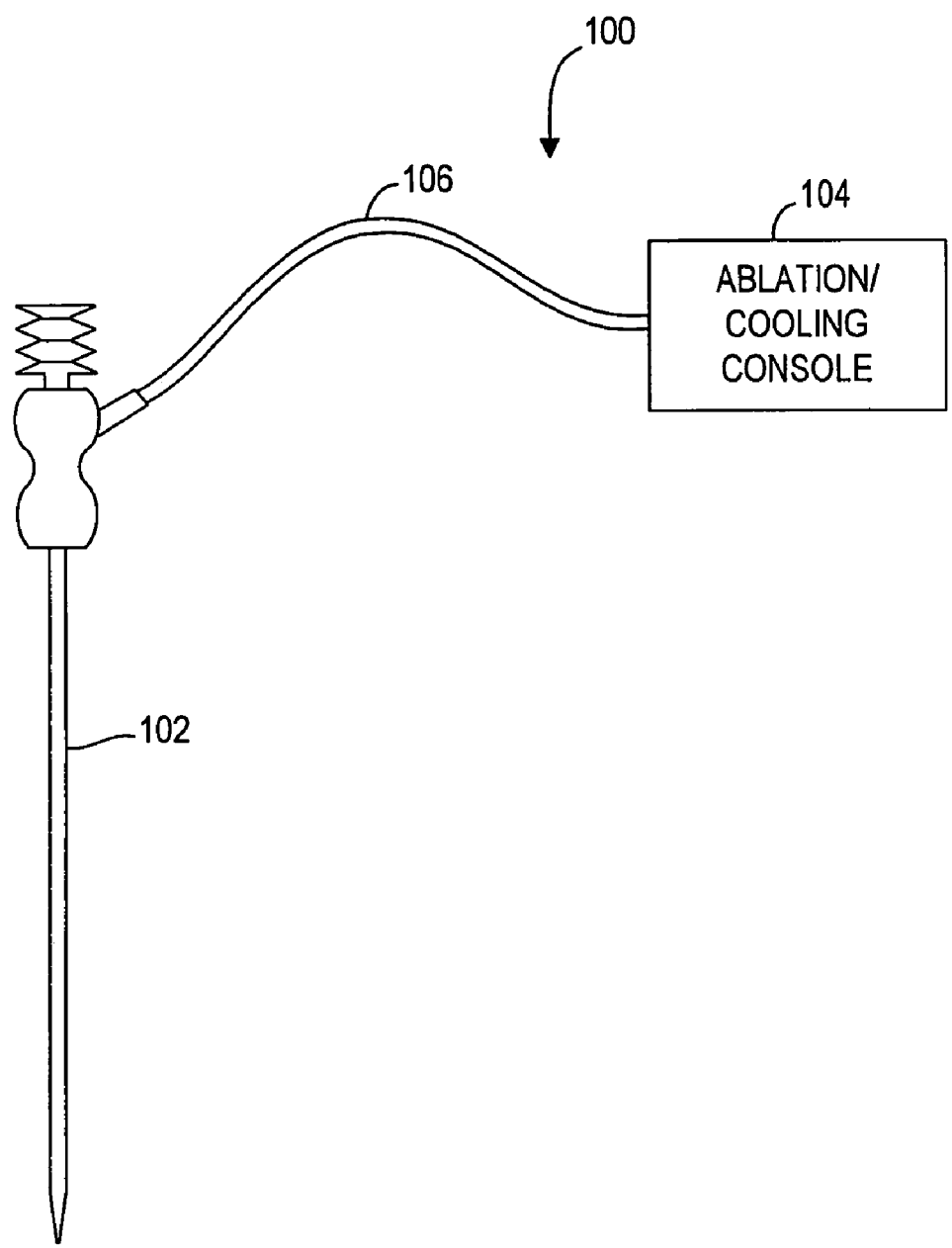
FIG. 1 is a plan view of an ablation system contructed in accordance with a preferred embodiment of the present invention.

Referring to FIG. 1, a tissue ablation system 100 constructed in accordance with a preferred embodiment of the present invention, will now be described. The tissue ablation system 100 generally comprises an ablation probe 102 configured for introduction into the body of a patient for ablative treatment of target tissue, an ablation/cooling console 104 configured for supplying both RF energy and cooling signals to the ablation probe 102 in a controlled manner, and a cable 106 electrically connecting the ablation probe 102 to the ablation/cooling console 104.

Figure 2:
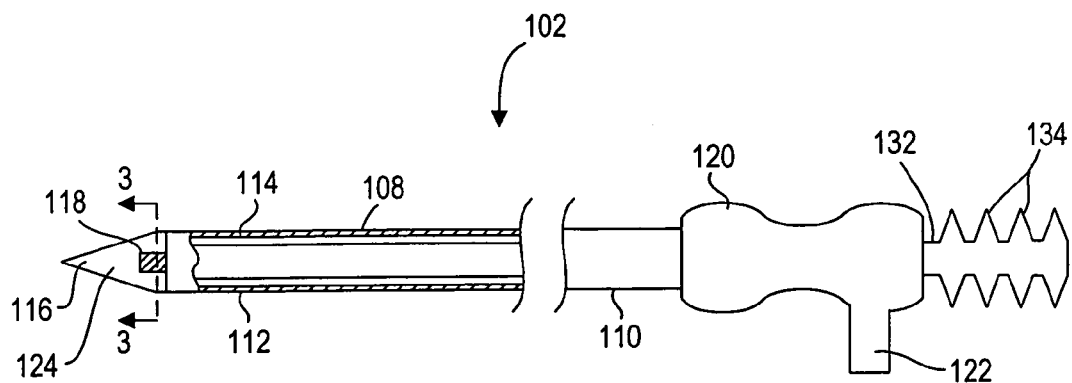
FIG. 2 is a partially cutaway side view of an ablation probe used in the ablation system of FIG. 1.

Referring now to FIG. 2, the ablation probe 102 will be described in further detail. The ablation probe 102 comprises an elongated shaft 108 having a proximal end 110, a distal end 112, and an internal axial lumen 114. The probe shaft 108 is preferably composed of a rigid or semi-rigid material, such that the probe shaft 108 can be introduced through solid tissue to a target tissue site. The distal end 112 of the probe shaft 108 comprises a tissue-penetrating tip 116, which allows the probe shaft 108 to be more easily introduced through tissue, while minimizing tissue trauma. Alternatively, the probe shaft 108 may be introduced through the tissue with the aid of a cannula and trocar assembly, in which case, the probe shaft 108 may be composed of a flexible material, and the distal end 112 may be blunted. The distal end 112 of the probe shaft 108 preferably carries a visualization marker 118 to allow the physician to identify the orientation of the ablation probe 102. The visualization marker 118 may be an ultrasound, MRI, RF signal reflector, or other visualization marker known to those of skill in the art.

In the preferred embodiment, the probe shaft 108 is composed of an electrically conductive material, such as stainless steel. In this case, the exterior surface of the probe shaft 108, with the exception of the distal tip 116, is preferably composed of an electrically insulative material (not shown). Alternatively, the probe shaft 108 may be composed of an electrically insulative material, such as a medical grade plastic, in which case, a separate insulative coating is not needed. The probe shaft 108 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm.

The ablation probe 102 further comprises a handle 120 mounted to the proximal end 110 of the probe shaft 108. The handle 120 is preferably composed of a durable and rigid material, such as medical grade plastic, and is ergonomically molded to allow a physician to more easily manipulate the ablation probe 102. The handle 120 comprises an electrical connector 122 with which the cable 106 (shown in FIG. 1) mates.

Figure 3:
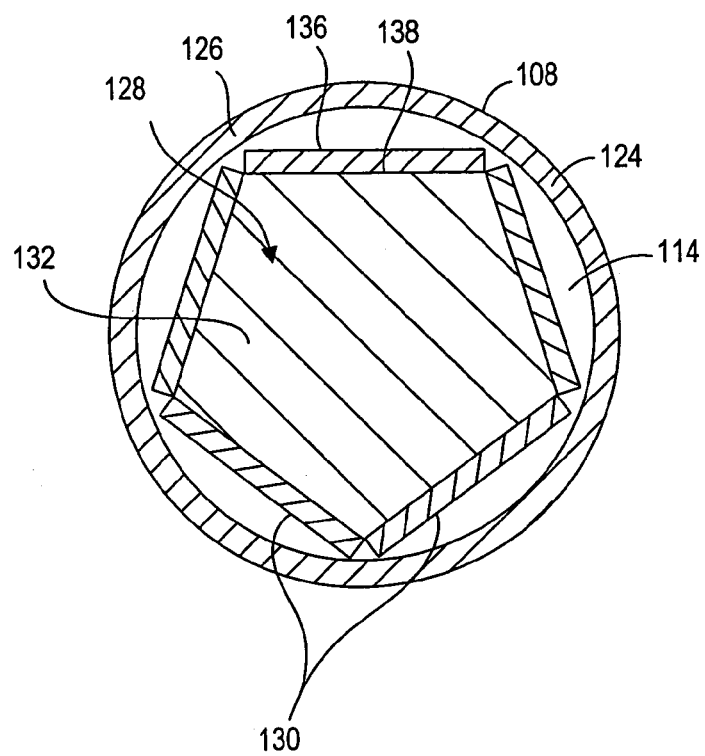
FIG. 3 is a cross-sectional view of the ablation probe of FIG. 2, taken along the line 3-3.

The ablation probe 102 further comprises an RF ablation electrode 124 carried by the distal end 112 of the probe shaft 108. In the preferred embodiment, the electrode 124 is formed by the exposed portion of the shaft distal tip 116. Alternatively, if the probe shaft 108 is composed of an electrically insulative material, the distal tip 116 can be coated with an electrically conductive material to form the electrode thereon, or a discrete ring electrode can be interference fit at the base of the distal tip 116. In this alternative case, a separate RF wire (not shown) will need to be routed from the electrode back through the shaft lumen 114. As best shown in FIG. 3, the ablation electrode 124 comprises a cylindrical hollow portion 126, the function of which will be described in further detail below.

The ablation probe 102 further comprises a heat sink 128 composed of a thermally conductive material, such as aluminum. The distal end of the heat sink 128 is disposed within the hollow portion 126 of the electrode 124. The ablation probe 102 further comprises a number of thermoelectric devices 130 (in this case, five) circumferentially arranged and mounted to the external distal surface of the heat sink 128. The heat sink 128 serves to dissipate unwanted heat absorbed by the thermoelectric devices 130 from the hollow portion 126 of the electrode 124. In particular, the heat sink 128 comprises a rod 132 that extends through the lumen 114 of the elongated shaft 108 and out from the handle 120, and cooling fins 134 formed at the proximal end of the heat sink rod 132 and exposed to the ambient air. The heat sink rod 132 has a pentagonal cross-sectional shape to provide mounting surfaces for the five respective thermoelectric devices 130. Of course, the cross-sectional shape of the heat sink rod will differ, depending on the number of thermoelectric devices 130 that are to be installed within the ablation probe 102. With the exception of the portion of the heat sink rod 132 on which the thermoelectric devices 130 are mounted, the exterior surface of the heat sink rod 132 comprises an electrically insulative coating (not shown) to provide electrical isolation from the RF energy conducting probe shaft 108. Alternatively, if a heat sink with cooling fins is not desirable, a thermoelectric device in the form of a tube can be disposed through the lumen 114 of the probe shaft 108. Atlhough the heat sink 128 is illustrated as being outside of the handle 120, it should be noted that the heat sink 128 is preferably contained within the handle 120, with the fins 134 extending partially or totally along the heat sink rod 132.

Each thermoelectric device 130 comprises a cold side 136, which is in thermal communication with the hollow portion 126 of the electrode 124, and a hot side 138, which is in thermal communication with the heat sink 128. Two signal wires (a positive wire and a negative wire, both not shown) are connected to each of the thermoelectric devices 130 and proximally extend through the lumen 114 of the probe shaft 108 to the electrical connector 122 on the handle 120. When the positive wire is coupled to a positive pole, and the negative wire is coupled to a negative pole, the cold and hot sides 136 and 138 of the thermoelectric devices 130 become cold and hot, respectively. As a result, thermal energy from the electrode 124 is absorbed by the cold sides 136 of the thermoelectric devices 130, which is then conducted to the hot sides 138 of the thermoelectric devices 130. The thermal energy emitted from the hot sides 138 of the thermoelectric devices 130 is then conducted through the heat sink rod 132 to the heat sink fins 134, where it dissipates into the ambient air.

Figure 4:
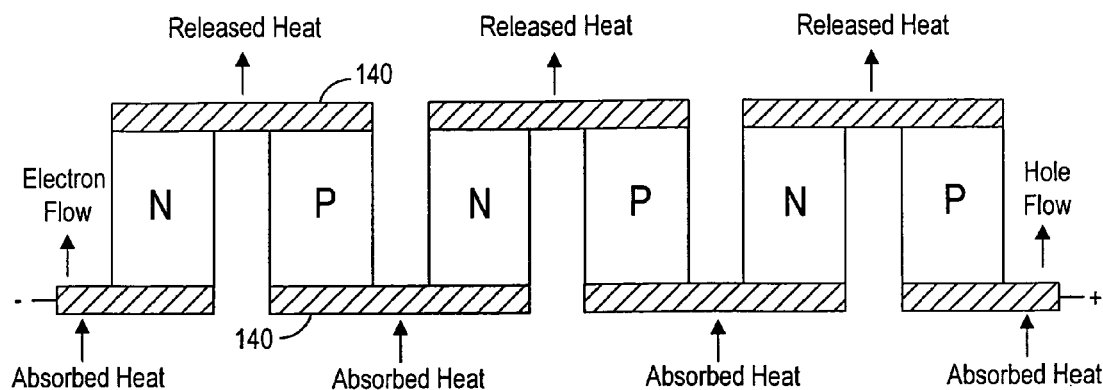
FIG. 4 is an electrical schematic of a type of thermoelectric cooling device that can be used in the ablation probe of FIG. 2.
Figure 5:
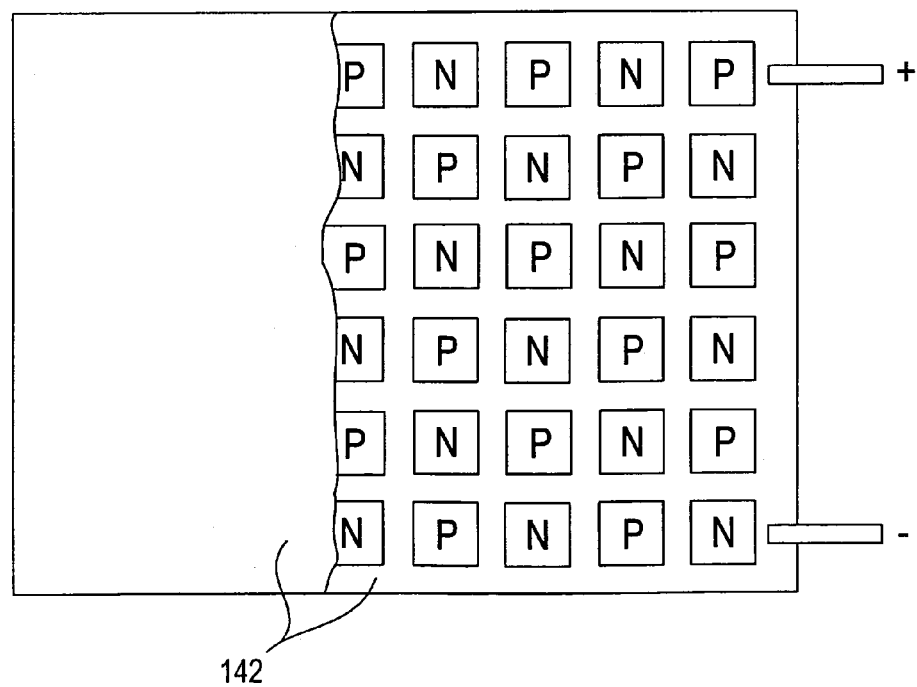
FIG. 5 is a partially cutaway top view of a thermoelectric cooling module that can be adapted to be used in the ablation probe of FIG. 2.

As illustrated in FIGS. 4 and 5, an example of a thermoelectric module is formed by a series of P- and N-doped pellets coupled together via electrical connectors 140, e.g, copper tabs. The exemplary thermoelectric module further comprises a pair of thin ceramic wafers 142 between which the P- and N-doped pellets are sandwiched. The ceramic wafers 142 add rigidity and are necessary for electrical insulation. The N-type pellets have an excess of electrons, while the P-type pellets has a deficit of electrons. The doped materials are preferably composed of bismuth-telluride semiconductor material.

The free (bottom) end of the P-type pellet is connected to a positive voltage potential (e.g., the positive signal wire) and the free (bottom) end of the N-type pellet is connected to ground (e.g., the negative signal wire). The positive charge carriers (i.e., the holes) in the P-type pellets are repelled by the positive voltage potential and attracted by the negative pole, whereas the negative charge carriers (electrons) in the N-type pellets are repelled by the negative potential and attracted by the positive pole. As the electrons move from a P-type pellet to an N-type pellet through an electrical connector 122, the electrons jump to a higher energy state, thereby absorbing thermal energy (cold side). Continuing through the lattice of material, the electrons flow from an N-type pellet to a P-type pellet through an electrical connector 122, dropping to a lower energy state and releasing energy as heat. The most common thermoelectric devices connect two hundred fifty-four alternating P- and N-type pellets, which can run from a 12 to 16 Volt DC supply and draw from 4 to 5 amps.

It should be noted that the thermoelectric module illustrated in FIGS. 4 and 5 is only an example and its detailed structure will vary depending on the geometry and size of the electrode in which it is to be mounted.

Referring back to FIG. 1, the ablation/cooling console is electrically connected via the cable 106 to the connector 122 on the handle 120. The electrical connector 122 comprises ablation/cooling connections that allows the ablation functionality of the ablation/cooling console 104 to be indirectly electrically coupled to the electrode 124 through the probe shaft 108, and the cooling functionality of the ablation/cooled console 104 to be indirectly coupled to the thermoelectric devices 130 via the insulated signal wires extending through the lumen 114 of the probe shaft 108.

The ablation/cooling console 104 may be similar to a conventional RF power supply (with the exception of the added cooling functionality described below) that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

RF current is preferably delivered from the ablation/cooling console 104 to the electrode 124 in a monopolar fashion, which means that current will pass from the electrode 124, which is configured to concentrate the energy flux in order to have an injurious effect on the adjacent tissue, and a dispersive electrode (not shown), which is located remotely from the electrode 124 and has a sufficiently large area (typically 130 cm$^2$ for an adult), so that the current density is low and non-injurious to surrounding tissue. In the illustrated embodiment, the dispersive electrode may be attached externally to the patient, e.g., using a contact pad placed on the patient's flank.

Figure 12:
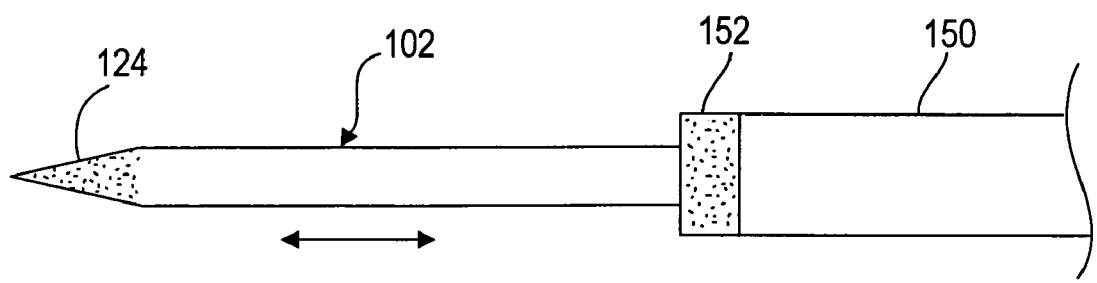
FIG. 12 is a cutaway side view of an ablation probe of FIG. 2 slidably disposed within a cannula to form a bipolar electrode arrangement.

Alternatively, RF current may be delivered from the ablation/cooling console 104 in a bipolar arrangement. For example, FIG. 12 illustrates the use of the ablation probe 102 within a bipolar assembly. In particular, the ablation probe 102 is reciprocatably disposed within a cannula 150 having a distally mounted electrode 152. A bipolar relationship between the electrode 124 on the ablation probe 102, and the electrode 152 on the cannula 150, can be formed by electrically coupling the respective poles of the ablation/cooling console 104 to the electrodes 124 and 152. The distance between the electrodes 124 and 152 can be adjusted by distally or proximally sliding the ablation probe 102 within the cannula 150, thereby providing a means for adjusting the ablation results. Optionally, the ablation probe 102 may be removable from the cannula 150 in order to provide a means for delivering therapeutic agents to the treated region before or after the ablation process. In an alternative embodiment, thermoelectric devices 130 can be located on the cannula 150 adjacent the electrode 152, in addition to, or rather than, placing the thermoelectric devices 130 on the ablation probe 102 adjacent the electrode 124. Additional details regarding the structure and operation of adjustable bipolar ablation probes are disclosed in U.S. patent application Ser. No. 10/828,032, which is expressly incorporated herein by reference.

The ablation/cooling console 104 additionally includes controlled cooling capability, and in particular, supplies DC voltage to the thermoelectric devices 130, which in turn, cool the electrode 124, and thus, the tissue in contact with the electrode 124. The ablation/cooling console 104 optionally has control circuitry (not shown) that turns the thermoelectric devices 130 off using temperature or impedance feedback, e.g., to maintain the treated tissue in a specific temperature range. As will be described in further detail below, the control circuitry is also capable of independently controlling the individual thermoelectric devices 130 in order to shape the resulting tissue ablation. The visualization marker 118 on the distal end 112 of the probe shaft 108 can be used by the physician to select which thermoelectric devices 130 are to be turned off or on.

Although the ablative and cooling control functionality has been described as being combined into a single console, i.e., the RF generator, these functionalities could be incorporated into two separate respective consoles, which would require separate pieces of equipment.

Thus, it can be appreciated that the use of the thermoelectric devices 130 provides a convenient means of cooling the tissue in contact with the electrode 124, thereby eliminating or minimizing tissue charring close to the electrode and maximizing energy dispersion distant from the electrode. The use of the thermoelectric devices 130 also allows the physician to selectively cool a portion of the tissue, since the thermoelectric devices 130 can be selectively and independently turned on and off. The selective cooling allows the physician to sculpt the shape of the lesion.

Having described the structure of the tissue ablation system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radio labeled tumor-specific probes), and the like. Preferred is the use of high resolution ultrasound of the tumor or other lesion being treated, either intra operatively or externally.

Figure 6A:
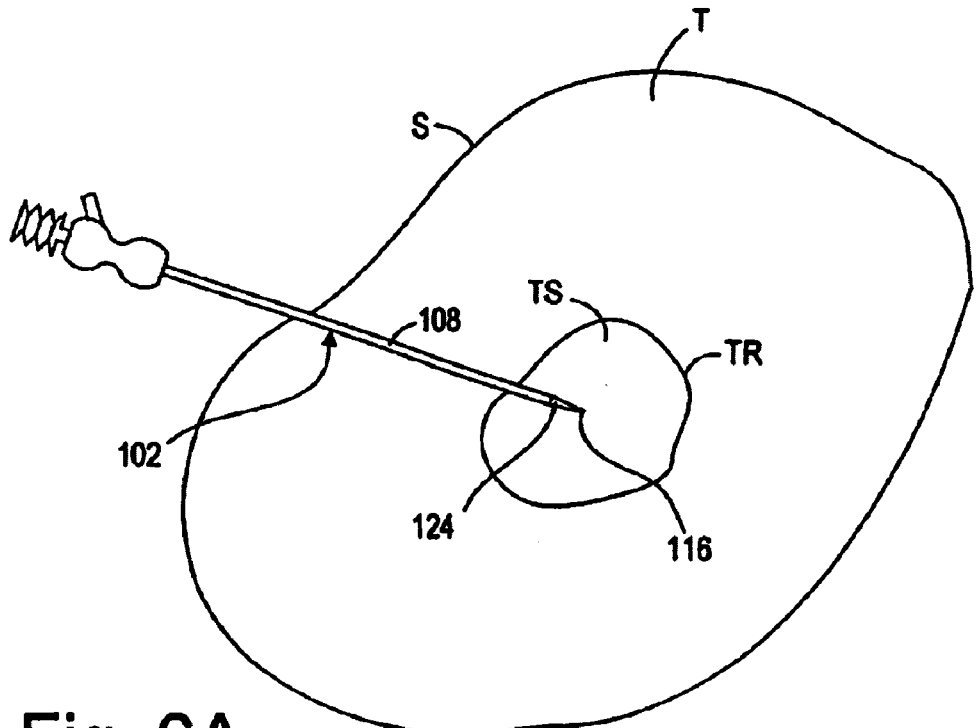
FIGS. 6A-6C are side views illustrating a method of ablating tissue using the ablation probe of FIG. 2.
Figure 6B:
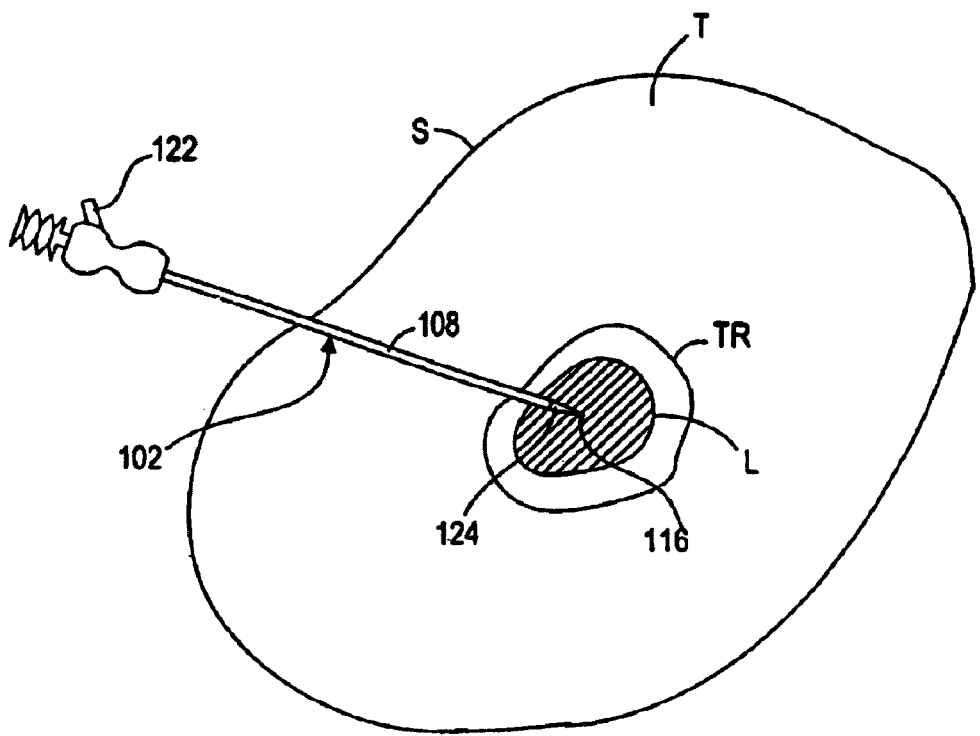
Figure 6C:
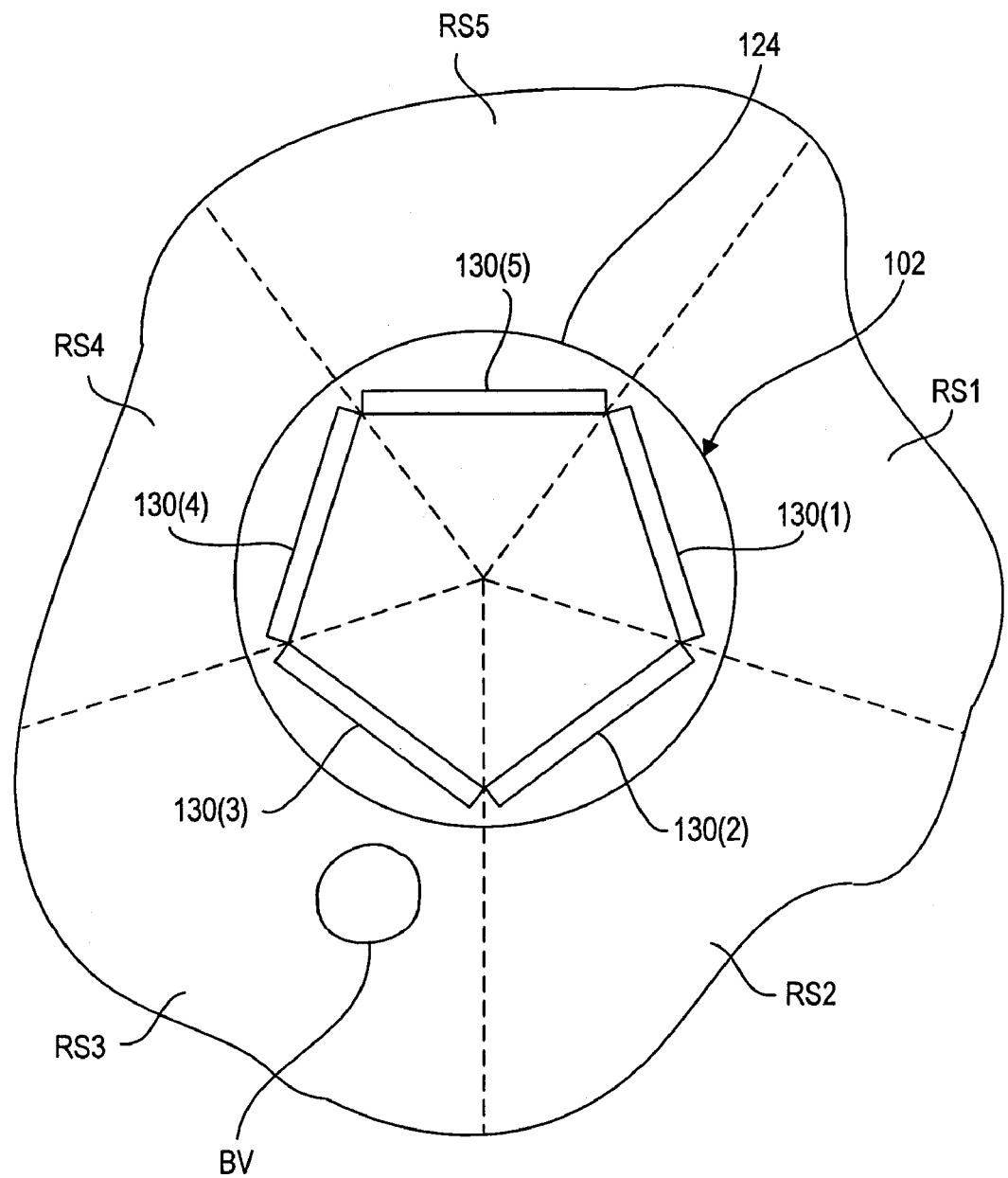

Referring now to FIGS. 6A-6C, the operation of the tissue ablation system 100 is described in treating a treatment region TR within tissue T located beneath the skin or an organ surface S of a patient. The ablation probe 102 is first introduced through the tissue T, so that the electrode 124 is located at a target site TS within the treatment region TR, as shown in FIG. 6A. This can be accomplished using any one of a variety of techniques. In the preferred method, ablation probe 102 is introduced to the treatment region TR percutaneously directly through the patient's skin or through an open surgical incision. In this case, the sharpened tip 116 of the probe shaft 108 facilitates introduction to the treatment region TR. In such cases, it is desirable that the probe shaft 108 be sufficiently rigid, i.e., have a sufficient column strength, so that it can be accurately advanced through tissue T. In other cases, the ablation probe 102 may be introduced using an internal stylet that is subsequently exchanged for the ablation probe 102. In this latter case, the probe shaft 108 can be relatively flexible, since the initial column strength will be provided by the stylet. More alternatively, a component or element may be provided for introducing the ablation probe 102 to the target ablation site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The ablation probe 102 can then be introduced through the sheath lumen, so that the distal end 112 of the probe shaft 108 advances from the sheath into the target ablation site TS.

Once the ablation probe 102 is properly positioned, the ablation/cooling console 104 (shown in FIG. 1) is then connected to the electrical connector 122, and then operated to transmit RF energy to the electrode 124, thereby ablating the treatment region TR, while simultaneously transmitting DC voltage to the thermoelectric devices 130, thereby cooling the treatment region TR, as illustrated in FIG. 6B. As a result, lesion L will be created, which will eventually expand to include the entire treatment region TR.

As described in further detail below, the thermoelectric devices 130 can be cycled on and off, or the amplitude of the DC voltage transmitted to the thermoelectric devices 130 can be reduced, in order to moderate the cooling effect on the electrode 124 and avoiding negation of the benefit of heating. It should also be noted that these techniques can be used to ramp down the cooling during the ablation process. That is, maximum cooling may be required at the beginning of the ablation process (when the electrode 124 is at its hottest) to avoid charring of the immediately adjacent tissue, whereas less cooling may be required near the end of the ablation process (when the electrode 124 is not as hot) to promote ablation of tissue away from the electrode 124. Notably, the use of thermoelectric devices lends itself well to this dynamically controlled cooling process.

As shown in FIG. 6C, the treatment region TR can be divided into a plurality of radial sectors RS 1-5 with each radial sector corresponding to a respective one of the circumferentially arranged thermoelectric devices 130. The electrode 124 is shown at the origin of the radial sectors, in which case, the thermal energy is radially conveyed from the electrode 124 into the radial tissue sectors to ablate the treatment region TR. The radial tissue sectors RS can be selectively cooled by turning off selected thermoelectric devices 130, so that they do not have a cooling effect on the tissue. For example, if the electrode 124 is adjacent a blood vessel BV, as shown in FIG. 6C, the thermoelectric device(s) 130 corresponding to the radial sector(s) 130 that contains the blood vessel BV (in this case, radial tissue sector RS(3)) can be turned off (in this case thermoelectric device (130 (3)), since the blood moving through the blood vessel BV already provides a cooling effect to that radial tissue sector RS(3). In this case, the thermoelectric devices 130(1), 130 (2), 130(4), and 130(5) are turned on, while the remaining thermoelectric device 130(3) corresponding to the blood cooled radial tissue sector RS(3) is turned off during the ablation process. In this manner, a more symetrical ablation can be performed by creating a uniform temperature gradient across the treatment region TR. Notably, reference to the visualization marker 118 (shown in FIG. 2) relative to the pertinent radial tissue sector will allow the physician to determine which of the thermoelectric device(s) to turn off.

It should be noted that the use of thermoelectric devices in ablation probes not only provides an effective means for cooling heat ablative electrodes, but also provides an independent means for cryogenically ablating tissue. For example, thermoelectric devices, such as those manufactured by Quasar Electronics Limited, located in Bishops Stortford, United Kingdom, maintain a generally uniform temperature difference of 59° C. between its respective cold and hot sides when operated at 13.5V, 4.4A. Thus, if the ablation probe carrying such thermoelectric devices is placed within a patient's body, the hot sides of the thermoelectric devices will be effectively maintained at body temperature (approximately, 37° C.), in which case, the cold sides of the thermoelectric devices can reach 37° C.-59° C.=-22° C.—well below freezing (0° C.). If the thermoelectric devices are placed into thermal contact with an RF electrode, the resulting ablation probe can be used to either hyperthermically or hypothermically ablate tissue via the electrode. For example, if the physician desires to hyperthermically ablate tissue, RF energy can be supplied to the electrode. In this case, the thermoelectric devices can be operated to cool the tissue as previously described herein. If, however, the physician desires to hypothermically ablate tissue, RF energy is not supplied to the electrode. Rather, the thermoelectric devices are operated to cryogenically cool the electrode, which in turn freezes the adjacent tissue.

The use of thermoelectric devices in ablation probes also provides a means for pre-heating an RF electrode. For example, prior to or during placement of the ablation probe within the patient's body, the polarity of the signal wires leading to the thermoelectric devices can be reversed, thereby reversing the hot and cold sides of the thermoelectric devices. As a result, the RF electrode will be heated by the reverse polarized thermoelectric devices. As another alternative arrangement, the heat ablative capability of the ablation probe can be provided solely by the thermoelectric devices. For example, if the thermoelectric devices are operated at 13.5V, 4.4A, the electrode could potentially be heated to a temperature of 37° C.+59° C.=96° C. In this case, the electrode need not have RF ablation capability, and the thermoelectric devices can be selectively turned on and off to sculpt the tissue ablation. The electrode can also be cryogenically cooled by the thermoelectric devices simply be reversing the polarity of the signal wires leading to the thermoelectric devices.

It should also be noted that a particular thermoelectric device, whether used for cooling or heating, need not be turned off or turned on through the entire ablation process. Instead, a thermoelectric device can be cycled with a uniform duty cycle during the ablation process in order to moderate the cooling effect of the thermoelectric devices. In this case, the thermoelectric devices may be operated with differing duty cycles. For example, returning to the example in FIG. 6, all of the thermoelectric devices 130 may be cycled on during at least a portion of the ablation process, but the remaining thermoelectric device 130(3) may be operated with a decreased duty cycle, so that the radial tissue sector RS3 is not over-cooled.

Alternatively, the thermal effect of the device can be controlled by adjusting the DC power supplied to it. For example, one thermoelectric device can be operated at 13.5V, 4.4A, to provide maximum cooling or heating of a radial tissue sector (depending on the polarity), and another thermoelectric device can be operated at 5V, 2A to provide less than maximum cooling or heating of another radial tissue sector.

Referring now to FIGS. 7 and 8, another preferred embodiment of an ablation probe 202 will be described. The ablation probe 202 generally comprises an elongated delivery cannula 204 and an inner probe 206 slidably disposed within the cannula 204. The cannula 204 has a proximal end 208, a distal end 210 with a sharpened distal tip 214, and a central lumen 212 (shown in FIG. 9) extending through the cannula 204. The cannula 204 may be rigid, semi-rigid, or flexible depending upon the designed means for introducing the cannula 204 to the target tissue. The cannula 204 is composed of a suitable material, such as plastic, metal or the like, and has a suitable length, typically in the range from 5 cm to 30 cm, preferably from 10 cm to 25 cm. If composed of an electrically conductive material, the cannula 204 is preferably covered with an insulative material. The cannula 204 has an outside diameter consistent with its intended use, typically being from 1 mm to 5 mm, usually from 1.3 mm to 4 mm. The cannula 204 has an inner diameter in the range from 0.7 mm to 4 mm, preferably from 1 mm to 3.5 mm. The cannula 204 is provided with a handle 216 to allow a physician to more easily grasp the proximal end of the ablation probe 202 when inserting the distal end into solid tissue, e.g., through the abdominal wall and liver tissue of a patient.

Referring further to FIG. 9, the inner probe 206 comprises a reciprocating deployment member 218, a distally mounted hollow cylindrical member 220, and an array 222 of tissue penetrating needle electrodes 224 circumferentially mounted within the cylindrical member 220. Like the cannula 204, the deployment member 218 and cylindrical member 220 are composed of a suitable material, such as plastic, metal or the like. A proximal plunger 226 is mounted to the deployment member 218, such that movement of the plunger 226 relative to the handle 216 provides for deployment of the electrode array 222 out of the distal end 210 of the cannula 204 (FIG. 8), and retraction of the electrode array 222 into the distal end 210 of the cannula 204 (FIG. 7). The plunger 226 comprises an electrical connector (not shown) with which the cable 106 from the ablation/cooling console 104 (shown in FIG. 1) mates. The electrical connector is indirectly electrically coupled to the electrode array 222 through the deployment member 218. The ablation/cooling console 104 may deliver RF ablation energy in a monopolar fashion, as previously described above.

Each of the individual needle electrodes 224 is in the form of a small diameter metal element, which can penetrate into tissue as it is advanced from a target site within the target region. When deployed from the cannula 204 (FIG. 8), the electrode array 222 is placed in a three-dimensional configuration that usually defines a generally ellipsoidal or spherical volume having a periphery with a maximum radius in the range from 0.5 to 4 cm. The needle electrodes 224 are resilient and pre-shaped to assume a desired configuration when advanced into tissue. In the illustrated embodiment, the needle electrodes 224 diverge radially outwardly from the cannula 204 in a uniform pattern, i.e., with the spacing between adjacent needle electrodes 224 diverging in a substantially uniform and/or symmetric pattern. In the illustrated embodiment, the needle electrodes 224 also evert proximally, so that they face partially or fully in the proximal direction when fully deployed.

More comprehensive details describing the general structure and operation of the ablation probes with deployable needle electrode arrays are disclosed in U.S. Pat. No. 6,575,967, which is incorporated by reference herein for all it teaches and describes.

Figure 10:
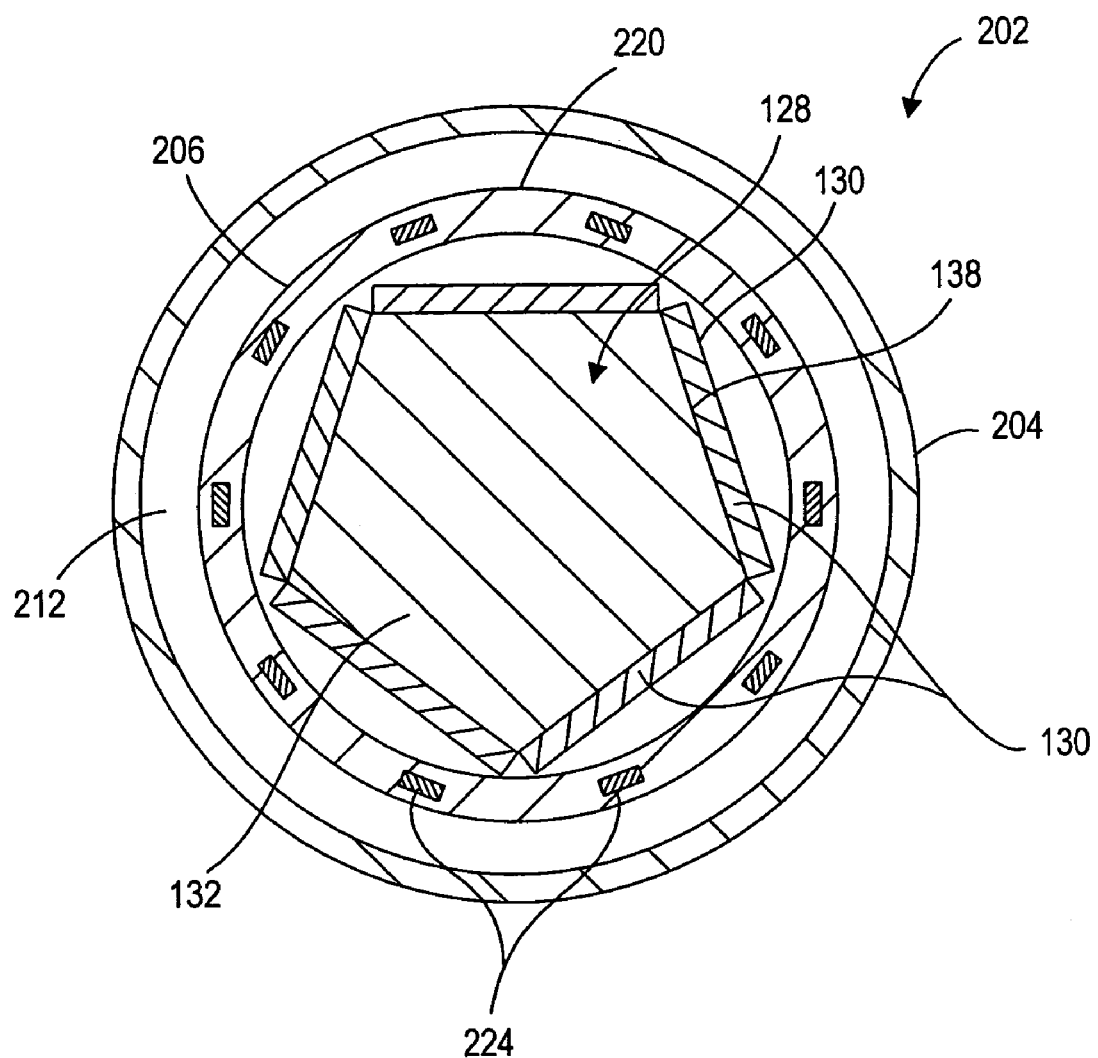
FIG. 10 is a cross-sectional view of the distal end of the ablation probe of FIG. 9, taken along the line 10-10.

In addition to the standard RF ablation capability, the ablation probe 202 has cooling functionality. To this end, and as best shown in FIG. 10, the inner probe 206 further comprises the previously described heat sink 128 and thermoelectric devices 130. The cold side 136 of each thermoelectric device 130 is in thermal communication with the cylindrical member 220, which, is in turn, in thermal communication with the needle electrodes 224. As a result, thermal energy from the electrode array 222 is absorbed by the cold sides 136 of the thermoelectric devices 130 via the cylindrical member 220, which is then conducted to the hot sides 138 of the thermoelectric devices 130. The thermal energy emitted from the hot sides 138 of the thermoelectric devices 130 are then conducted through the heat sink rod 132 to the heat sink fins 134, where it dissipates into the ambient air. The ablation/cooling console 104 (shown in FIG. 1) is electrically coupled to the electrical connector 122 on the plunger 226, which is in turn, electrically coupled to the signal wires (not shown) connected to the thermoelectric devices 130.

Alternatively, rather than locating the thermoelectric devices 130 within the cylindrical member 220, they can be mounted on the proximal ends of the needle electrodes 224. Or the needle electrodes 224, themselves, can be thermoelectric devices 130.

Figure 11A:
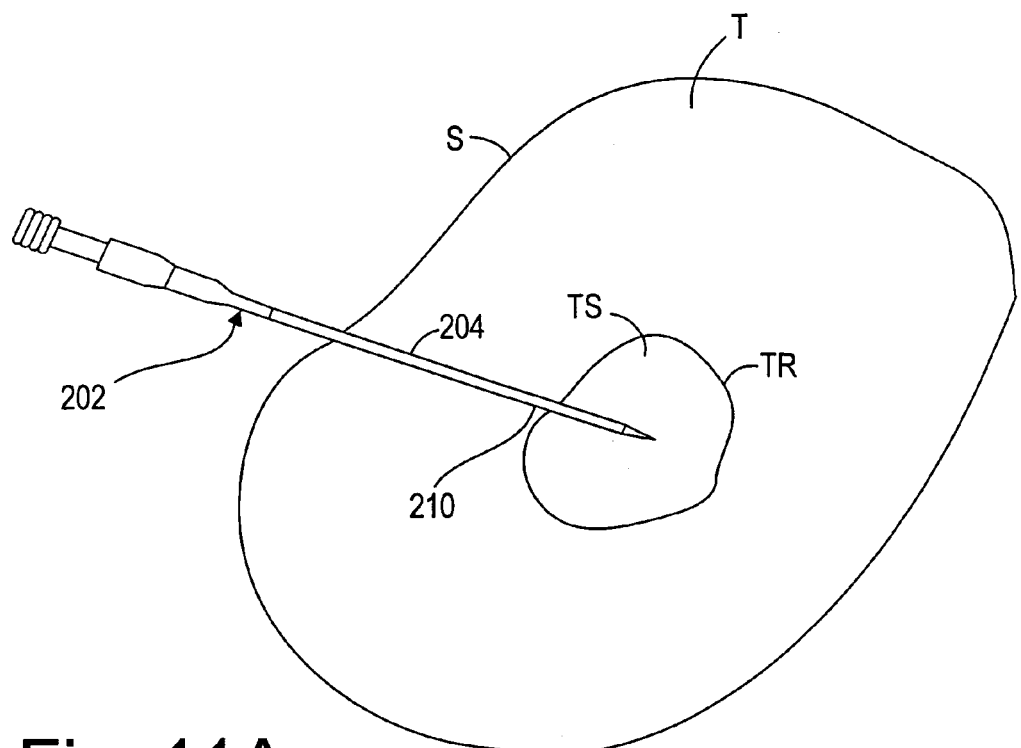
FIGS. 11A-11C are side views illustrating a method of ablating tissue using the ablation probe of FIG. 7.
Figure 11B:
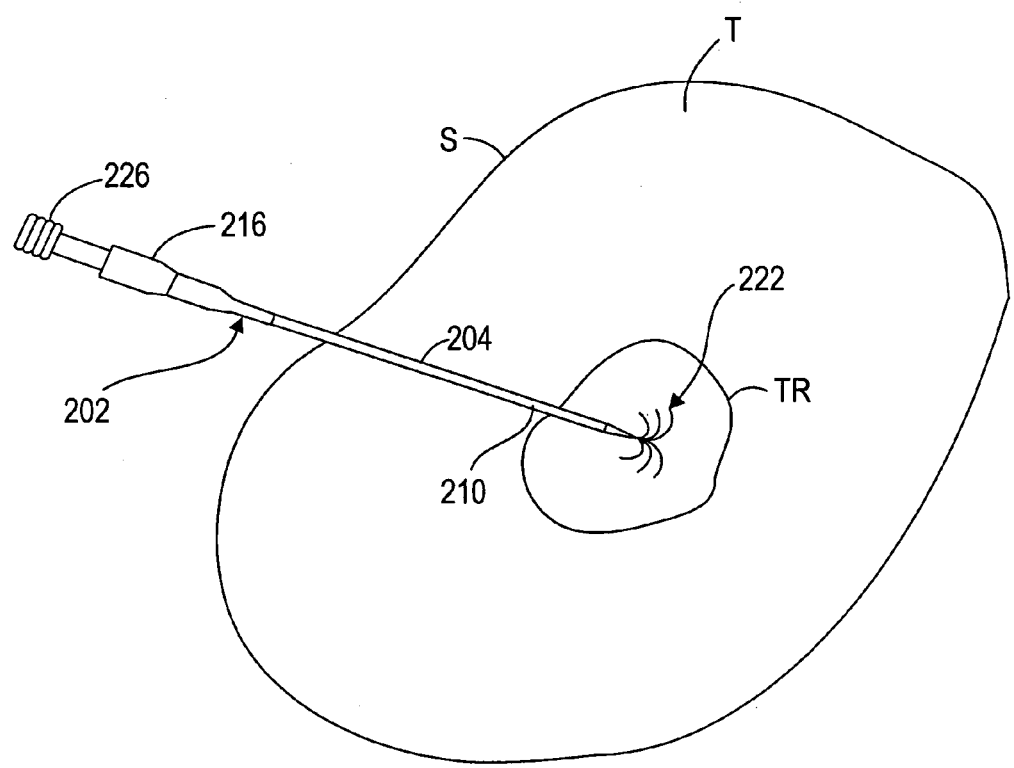
Figure 11C:
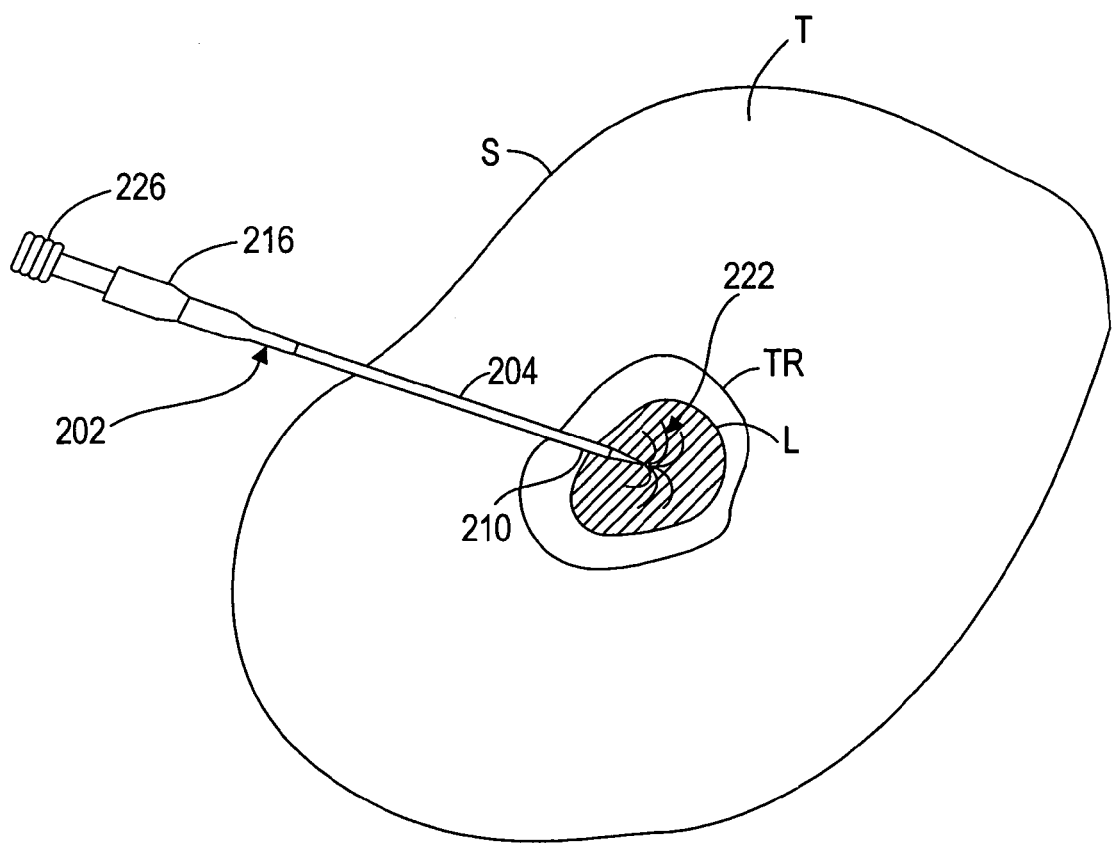

Referring now to FIGS. 11A-11C, the operation of the tissue ablation system 100, using the ablation probe 202, is described in treating a treatment region TR within tissue T located beneath the skin or an organ surface S of a patient. In any one of the same manners described above with respect to the ablation probe 102, the ablation probe 202 is first introduced within the treatment region TR, so that the distal end 210 of the cannula 204 is located at the target site TS, as shown in FIG. 11A. After the cannula 204 is properly placed, the plunger 226 is distally moved relative to the handle 216, thereby distally advancing the deployment member 218 of the inner probe 206 (shown in FIG. 10) to deploy the electrode array 222 radially outward from the distal end 210 of the cannula 204, as shown in FIG. 11B. The ablation/cooling console 104 is then connected to the electrical connector 122 on the inner probe 206, and then operated to create a lesion L within the treatment region TR, as illustrated in FIG. 11C. During the ablation process, the thermoelectric devices 130 may be operated to cool the treatment region TR near the electrodes 224, thereby providing for a more efficient heat ablation of tissue located further from the electrodes 224.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed:

1. An ablation probe, comprising:
   an elongated member;
   a heat ablative element mounted to a distal end of the elongated member; and
   a plurality of independently controllable thermoelectric cooling devices mounted to the elongated member in thermal communication with the ablative element.

2. The ablation probe of claim 1, wherein the elongated member is rigid.

3. The ablation probe of claim 1, wherein the thermoelectric devices are in direct contact with the ablative element.

4. The ablation probe of claim 1, wherein the ablative element is a radio frequency (RF) electrode.

5. The ablation probe of claim 1, wherein the ablative element comprises a plurality of tissue penetrating needle electrodes.

6. The ablation system of claim 1, wherein the thermoelectric devices are configured for absorbing heat from the ablative element.

7. The ablation probe of claim 1, further comprising a heat sink thermally coupled to the thermoelectric devices.

8. The ablation probe of claim 7, wherein the heat sink comprises a heat sink rod that extends through the elongated member, and a plurality of cooling fins formed at a proximal end of the heat sink rod.

9. The ablation probe of claim 7, wherein each of the thermoelectric devices comprises a cold side in thermal communication with the ablative element and a hot side in thermal communication with the heat sink.

10. An ablation system, comprising:
    the ablation probe of claim 1;
    thermal control circuitry electrically coupled to the thermoelectric devices the control circuitry configured for independently transmitting a signals to the thermoelectric devices whereby the thermoelectric devices cools the ablative element.

11. The ablation system of claim 10, further comprising an ablation source coupled to the ablative element.

12. The ablation system of claim 11, further comprising a console containing the thermal control circuitry and ablation source.

13. An ablation probe, comprising:
    an elongated member;
    a heat ablative element mounted to a distal end of the elongated member, the ablative element having a hollow cylindrical portion; and
    a plurality of discrete, independently controllable, cooling devices circumferentially distributed around an inner surface of the cylindrical portion.

14. The ablation probe of claim 13, wherein the elongated member is rigid.

15. The ablation probe of claim 13, wherein the cooling devices are thermoelectric cooling devices.

16. The ablation probe of claim 13, wherein the ablative element is a radio frequency (RE) electrode.

17. The ablation probe of claim 13, wherein the ablative element is a tissue-penetrating electrode.

18. The ablation system of claim 13, wherein the cooling devices are configured for absorbing heat from the ablative element.

19. The ablation probe of claim 13, further comprising a heat sink thermally coupled to the cooling devices.

20. The ablation probe of claim 19, wherein the heat sink comprises a heat sink rod that extends through the elongated member, and a plurality of cooling fins formed at a proximal end of the heat sink rod.

21. An ablation system, comprising:
    the ablation probe of claim 13; and
    thermal control circuitry configured for independently controlling the respective cooling devices, whereby the cooling devices cool the ablative element.

22. The ablation system of claim 21, further comprising an ablation source coupled to the ablative element.

23. The ablation system of claim 22, further comprising a console containing the thermal control circuitry and ablation source.

24. An ablation probe, comprising:
an elongated member;
a heat ablative element mounted to a distal end of the elongated member; and
a plurality of discrete, independently controllable, circumferentially distributed cooling devices in thermal communication with the ablative element.

25. The ablation probe of claim 24, wherein the elongated member is rigid.

26. The ablation probe of claim 24, wherein the cooling devices are thermoelectric cooling devices.

27. The ablation probe of claim 24, wherein the cooling devices are in direct contact with the ablative element.

28. The ablation probe of claim 24, wherein the ablative element is a radio frequency (RF) electrode.

29. The ablation probe of claim 24, wherein the ablative element is a tissue-penetrating electrode.

30. The ablation probe of claim 24, further comprising a heat sink thermally coupled to the cooling devices.

31. The ablation probe of claim 30, wherein the heat sink comprises a heat sink rod that extends through the elongated member, and a plurality of cooling fins formed at a proximal end of the heat sink rod.

32. An ablation system, comprising:
the ablation probe of claim 24; and
thermal control circuitry configured for independently controlling the respective cooling devices, whereby the cooling devices cool the ablative element.

33. The ablation system of claim 32, further comprising an ablation source coupled to the ablative element.

34. The ablation system of claim 33, further comprising a console containing the thermal control circuitry and ablation source.

* * * * *